US008814286B2

(12) United States Patent
Ward et al.

(10) Patent No.: US 8,814,286 B2
(45) Date of Patent: Aug. 26, 2014

(54) SIDE ACCESS STORAGE RACK FOR COLD STORAGE UNITS (75) Inventors: Dennis D. Ward, Vincent, OH (US); John P. Hutchinson, Marietta, OH (US); Brian E. Schott, Marietta, OH (US)

(73) Assignee: Thermo Fisher Scientific (Asheville) LLC, Asheville, NC (US)

( * ) Notice: Subject to any disclaimer, the term of this patent is extended or adjusted under 35 U.S.C. 154(b) by 60 days.

(21) Appl. No.: 13/488,619

(22) Filed: Jun. 5, 2012

(65) Prior Publication Data
US 2013/0320832 A1  Dec. 5, 2013

(51) Int. Cl.
A47B 96/04 (2006.01)
A47B 87/00 (2006.01)
A47B 43/00 (2006.01)

(52) U.S. Cl.
USPC ............ 312/404; 312/108; 312/257.1

(58) Field of Classification Search
CPC ........ A47B 43/02; A47B 47/06; A47B 96/04; F25D 25/00; F25D 25/024; F25D 23/025
USPC ............ 312/107, 108, 198, 201, 404, 407, 312/407.1, 265.5, 293.1, 293.2, 293.3; 211/184; 62/252; 232/24, 44, 45; 229/120.16, 120.17; 220/507, 553, 557
See application file for complete search history.

(56) References Cited

U.S. PATENT DOCUMENTS

| | | | |
|---|---|---|---|
| 654,660 A * | 7/1900 | Markline | 312/307 |
| 1,014,329 A * | 1/1912 | Pons | 62/326 |
| 1,589,064 A * | 6/1926 | Gearhart | 62/382 |
| 2,166,018 A * | 7/1939 | Palmer | 220/507 |
| 2,506,448 A * | 5/1950 | Gregor | 62/159 |
| 2,797,819 A * | 7/1957 | Lowmaster | 211/135 |
| 3,837,299 A * | 9/1974 | McClellan | 109/56 |
| 3,866,435 A * | 2/1975 | Frank et al. | 62/382 |
| 3,945,557 A * | 3/1976 | Graham, Jr. | 229/120.24 |
| 4,062,302 A * | 12/1977 | Krizan | 108/60 |
| 4,111,353 A * | 9/1978 | Collins et al. | 229/120.16 |
| 4,153,311 A * | 5/1979 | Takahashi | 312/107 |
| 4,317,607 A * | 3/1982 | Gomolka | 312/236 |

(Continued)

OTHER PUBLICATIONS

Thermo Fisher Scientific Inc., "Thermo Scientific CryoExtra High-Efficiency Cryogenic Storage," Fisher Scientific Brochure No. BNO130126, CSCROEXTRA-CCG 0112 (4 pages), 2012.

(Continued)

Primary Examiner — Daniel Rohrhoff
Assistant Examiner — Kimberley S Wright
(74) Attorney, Agent, or Firm — Wood, Herron & Evans, LLP (57) ABSTRACT A cold storage unit includes a side access storage rack for holding storage boxes. The storage rack includes a housing with a top wall, a bottom wall, and a rear side wall extending between the top and bottom walls to define a storage space. The storage rack also includes a plurality of vertical dividers extending from the rear side wall and a horizontal shelf configured to be engaged with the plurality of vertical dividers to split the storage space into a grid of box receptacles for the storage boxes. The horizontal shelf includes an angled front portion that is bent and is configured to frictionally engage divider slots in the vertical dividers to thereby hold the horizontal shelf in position with respect to the housing. This frictional engagement simplifies manufacturing and improves the functionality of the storage rack.

14 Claims, 8 Drawing Sheets

(56) References Cited

U.S. PATENT DOCUMENTS

| | | | | |
|---|---|---|---|---|
| 5,031,974 | A | * | 7/1991 | Feucht et al. ............... 312/263 |
| 5,040,690 | A | * | 8/1991 | van der Schoot ............ 211/135 |
| 5,299,863 | A | * | 4/1994 | Albright, Jr. ................ 312/404 |
| 5,600,966 | A | * | 2/1997 | Valence et al. ................ 62/440 |
| 5,605,047 | A | * | 2/1997 | Park et al. ..................... 62/3.6 |
| 5,605,389 | A | * | 2/1997 | Kelly et al. .................. 312/258 |
| 5,910,163 | A | * | 6/1999 | Schlamp ......................... 62/256 |
| 6,220,682 | B1 | * | 4/2001 | Vertullo .................. 312/334.28 |
| 6,626,508 | B1 | * | 9/2003 | Hase et al. .................... 312/236 |
| 7,216,773 | B2 | * | 5/2007 | Golias et al. ................. 211/184 |
| 7,318,321 | B2 | * | 1/2008 | Grassmuck et al. ............ 62/255 |
| 7,452,039 | B1 | * | 11/2008 | Golias et al. ............... 312/257.1 |
| 8,099,967 | B2 | | 1/2012 | Jia |
| 8,287,060 | B1 | * | 10/2012 | Golias et al. ................. 312/351 |
| 8,434,838 | B2 | * | 5/2013 | Zabbatino ..................... 312/404 |
| 8,496,308 | B2 | * | 7/2013 | Zabbatino ..................... 312/407 |
| 2005/0109722 | A1 | * | 5/2005 | Golias et al. ................. 211/135 |
| 2009/0309464 | A1 | * | 12/2009 | Schwartz ...................... 312/111 |
| 2012/0206029 | A1 | * | 8/2012 | Zabbatino ..................... 312/404 |
| 2012/0209763 | A1 | * | 8/2012 | Zabbatino ....................... 705/39 |

OTHER PUBLICATIONS

VWR® Low and Ultra-Low Temperature Feezers, Brochure 1011 7M Lit. No. 92939, Jan. 2012 (8 pages), 2012.

Thermo Fisher Scientific, Inc., "Thermo Scientific Revco Ultra-low Temperature Feezers" Brochure BRCSREVCOULT 0811 (32 pages), 2011.

Fisher Scientific, "Isotempe®-86° Freezers," Fisher Scientific Brochure No. BN0630113, BRCSISOULT Jul. 2011 (8 pages), 2010.

Thermo Fisher Scientific Inc., "New! Thermo Scientific TS Series Ultra-Low Temperature Freezers," BRCSTSULT 0811 (28 pages), 2011.

Thermo Fisher Scientific Inc., "Thermo Scientific Cryopreservation Equipment," Brochure BRCSCRYO 0310 (36 pages), 2010.

Thermo Fisher Scientific Inc., "New! Thermo Scientific HERAfreeze Ultra-Low Temperature Feezers," Brochure BRCSHERAULT 0811 (28 pages), 2011.

Thermo Fisher Scientific Inc., "New! Thermo Scientific Forma Ultra-Low Temperature Freezers," Brochure BRCSFULT 0711 (28 pages), 2011.

Thermo Fisher Scientific Inc., "Thermo Scientific CryoExtra High-Efficiency Cryogenic Storage," Fisher Scientific Brochure No. BN0130126, CSCRYOEXTRA-CCG, Jan. 2012 (4 pages).

Thermo Fisher Scientific Inc., "New! Thermo Scientific Forma Ultra-Low Temperature Freezers," Brochure BRCSFULT, Jul. 2011 (28 pages).

Thermo Fisher Scientific, Inc., "Thermo Scientific Revco Ultra-low Temperature Feezers" Brochure BRCSREVCOULT, Aug. 2011 (32 pages).

Fisher Scientific, "Isotempe®-86° Freezers," Fisher Scientific Brochure No. BN0630113, BRCSISOULT, Jul. 2011 (8 pages).

Thermo Fisher Scientific Inc., "New! Thermo Scientific TS Series Ultra-Low Temperature Freezers," BRCSTSULT, Aug. 2011 (28 pages).

Thermo Fisher Scientific Inc., "Thermo Scientific Cryopreservation Equipment," Brochure BRCSCRYO, Mar. 2010 (36 pages).

Thermo Fisher Scientific Inc., "New! Thermo Scientific HERAfreeze Ultra-Low Temperature Feezers," Brochure BRCSHERAULT, Aug. 2011 (28 pages).

* cited by examiner

SIDE ACCESS STORAGE RACK FOR COLD STORAGE UNITS

FIELD OF THE INVENTION

The present invention relates generally to storage racks and, more particularly, to side access storage racks used with cold storage units such as upright freezers.

BACKGROUND OF THE INVENTION

Cold storage units such as freezers and dewars are used for various purposes, including the storage of biological samples over short and long periods of time. For example, biological materials for transplantation such as blood, tissue, or plasma may require storage for short periods of time before use. In another example, biological cells such as DNA samples may be stored for longer periods of time. Conventional cold storage units may be cooled by mechanical refrigeration circuits or by other methods, including the provision of liquid nitrogen ("LN2"). One type of cold storage unit used to store biological samples is known as an "ultra-low temperature freezer" ("ULT"), which is used to cool its inner storage chamber to relatively low temperatures such as about −80° C. or lower, for example.

Known cold storage units are configured to contain a plurality of storage boxes supported on different types of storage racks within a cooled cabinet. One type of storage rack referred to as a side access storage rack is configured to contain a rectangular array of storage boxes and provide access to these storage boxes through an open front side of the storage rack. To this end, this type of side access storage rack includes a housing with a top wall and a bottom wall connected at the ends by first and second end walls. The top and bottom walls are formed from one piece of sheet material connected by a rear side wall that extends between the top wall and the bottom wall. The first and second end walls may also be formed from the same piece of sheet material and bent into position such that the first and second end walls are spot welded to the top and bottom walls.

A plurality of vertical dividers extend from the rear side wall and are aligned in a series between the first and second end walls. Similarly, a plurality of horizontal shelves are inserted into engagement with the first and second end walls and with the plurality of vertical dividers, thereby splitting the space within the storage rack into a grid of box receptacles, with each box receptacle being sized to receive a storage box therein. The side access storage rack defines an open front side through which the storage boxes on the plurality of horizontal shelves may be retrieved from and returned to the storage rack.

A horizontal shelf 300 used with the conventional side access storage rack described above is shown in FIG. 8. The shelf 300 includes a planar shelf surface 302 and a pair of connection tabs 304 bent upwardly from the shelf surface 302 at opposed ends thereof. The shelf surface 302 includes a plurality of shelf slots 306 configured to receive corresponding vertical dividers when the shelf 300 is inserted into the housing of the side access storage rack. The connection tabs 304 include snap connection notches 308 that are configured to snap into engagement with corresponding projecting tabs (not shown) extending inwardly from the first and second end walls of the housing. In one example, these projecting tabs are formed in a separate end plate which is spot welded to each of the first and second end walls, thereby increasing the number of parts needed to form the side access storage rack. These snap connection notches 308 and the corresponding projecting tabs must also be specially machined from the corresponding elements of the storage rack before assembly.

Figure 8:
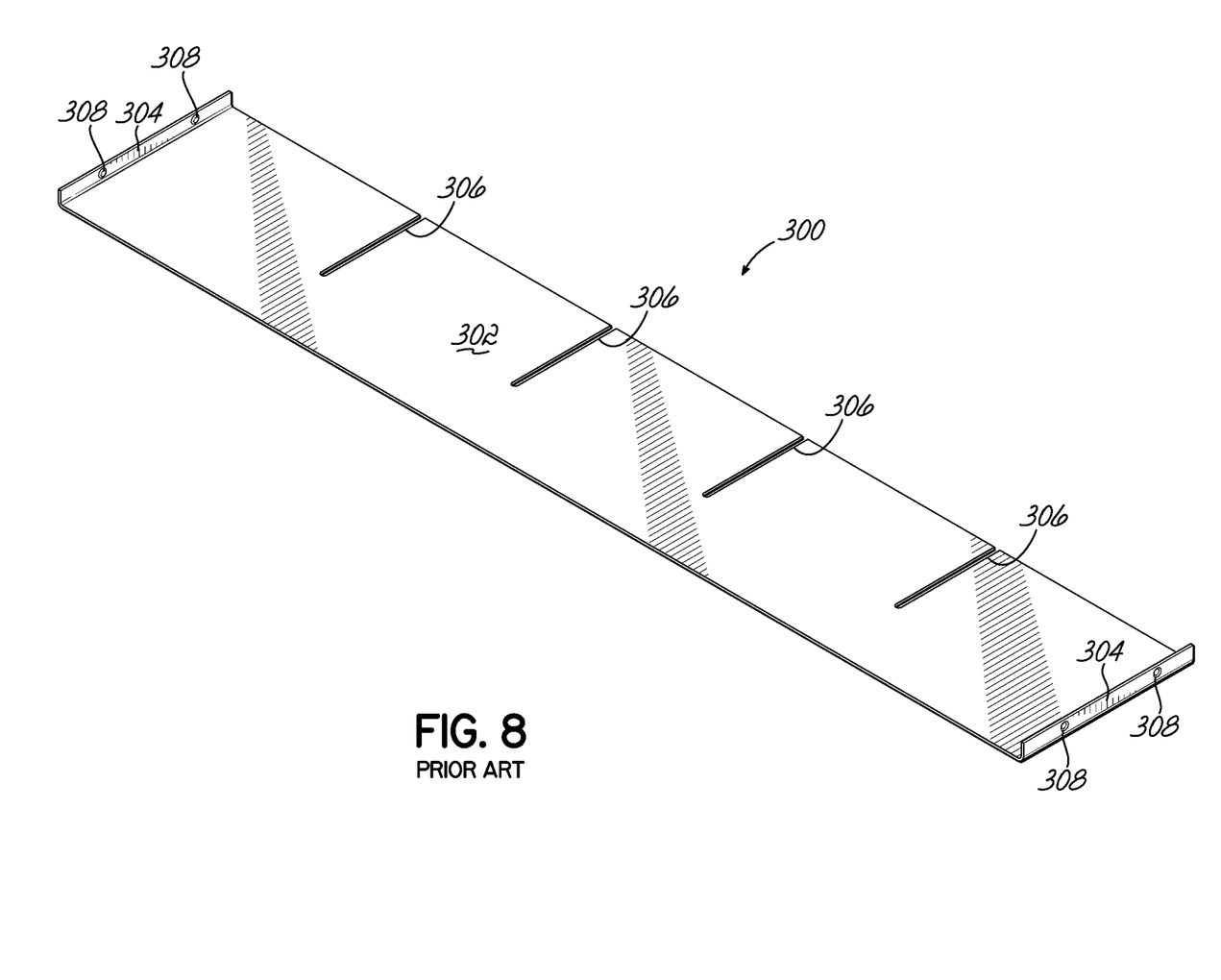
FIG. 8 is a perspective view of a horizontal shelf used with a prior art side access storage rack.

This additional machining adds manufacturing time and expense to the overall assembly of the side access storage rack. When the projecting tabs are formed in separate end plates connected to the first and second end walls, the end plates add additional weight and materials cost to the side access storage rack. Furthermore, correctly snapping the shelves 300 into position requires additional assembly time. Once the side access storage rack is assembled, the horizontal shelves 300 are held primarily by the plurality of projecting tabs, which are designed with some resiliency to snap into engagement with the snap connection notches 308. Consequently, the horizontal shelves 300 are prone to small vibrations resulting at least in part from this resiliency and also in part from the long lengths between support points when the side access storage rack is moved. Even though the horizontal shelves 300 are securely held within the housing, the vibrations may provide the undesirable impression that the side access storage rack is unstable or poorly assembled.

There is a need, therefore, for a side access storage rack for use with a cold storage unit that improves the manufacturing process while providing improved performance compared to conventional side access storage racks.

SUMMARY OF THE INVENTION

In one embodiment according to the present invention, a side access storage rack for holding storage boxes within a cold storage unit includes a housing having a top wall, a bottom wall, and a rear side wall extending between the top and bottom walls. The housing defines a storage space accessible through an open front side of the housing. The storage rack also includes a plurality of vertical dividers extending from the rear side wall toward the open front side of the housing, each vertical divider including a front edge and a plurality of divider slots extending rearwardly from the front edge. The storage rack also includes a horizontal shelf including opposing front and rear edges. A plurality of shelf slots extend forwardly from the rear edge and an angled front portion is bent adjacent to the front edge. The horizontal shelf is engaged with the plurality of vertical dividers by sliding the horizontal shelf into the divider slots and sliding the vertical dividers into the shelf slots until the angled front portion of the shelf is wedged into frictional engagement with the divider slots. The frictional engagement holds the horizontal shelf in position such that the horizontal shelf and the plurality of vertical dividers split the storage space into a grid of box receptacles configured to receive the storage boxes. The frictional engagement of the horizontal shelf at multiple locations along its length simplifies the manufacturing of the side access storage rack and advantageously forms a rigid coupling that limits any vibration of the shelf during use of the side access storage rack.

In one aspect, the horizontal shelf includes a blocking lip extending upwardly from the shelf at the rear edge. The blocking lip blocks twisting or sliding movement of the storage boxes through the rear side wall of the housing. In another aspect, the angled front edge of the horizontal shelf is bent downwardly from the shelf such that the angled front edge defines a beveled opening for guiding storage boxes into the box receptacle.

In another aspect, the housing further includes first and second end walls extending between the top and bottom walls at opposing edges of the rear side wall. The storage space defined by the housing is therefore box-shaped. The horizontal shelf is spaced from each of the first and second end walls when inserted into frictional engagement with the plurality of vertical dividers, thereby enabling the horizontal shelf to be completely supported by the frictional engagement. A handle for manually moving the storage rack is pivotally coupled to one of the first and second end walls, but the top wall, bottom wall, and first and second end walls are solid planar members except at this pivotal coupling to the handle. In one example, the top wall, the bottom wall, the rear side wall, the first and second end walls, and the plurality of vertical dividers are formed from bending a single sheet of material.

In yet another aspect, the side access storage rack includes a plurality of horizontal shelves each including a plurality of shelf slots and an angled front portion. The horizontal shelves may be inserted into different sets of the plurality of divider slots in the vertical dividers to reconfigure the vertical height of the box receptacles formed in the storage space. For example, the horizontal shelves may be repositioned to adjust the vertical height from 2 inches for each shelf to 3 inches for each shelf to accommodate differently-sized storage boxes.

According to another embodiment, a cold storage unit for storing a plurality of storage boxes includes a cabinet and at least one side access storage rack. The cabinet includes an opening with a door and a cooled interior space. The side access storage rack is configured to be stored in the cooled interior space and includes a housing having a top wall, a bottom wall, and a rear side wall extending between the top and bottom walls. The housing defines a storage space accessible through an open front side of the housing. The storage rack also includes a plurality of vertical dividers extending from the rear side wall toward the open front side of the housing, each vertical divider including a front edge and a plurality of divider slots extending rearwardly from the front edge. The storage rack also includes a horizontal shelf including opposing front and rear edges. A plurality of shelf slots extend forwardly from the rear edge and an angled front portion is bent adjacent to the front edge. The horizontal shelf is engaged with the plurality of vertical dividers by sliding the horizontal shelf into the divider slots and sliding the vertical dividers into the shelf slots until the angled front portion of the shelf is wedged into frictional engagement with the divider slots. The frictional engagement holds the horizontal shelf in position such that the horizontal shelf and the plurality of vertical dividers split the storage space into a grid of box receptacles configured to receive the storage boxes.

In another embodiment according to the invention, a method of manufacturing a side access storage rack for holding storage boxes within a cold storage unit is provided. The method includes providing a flat sheet of material sized to define a housing including a rear side wall, a top wall, and a bottom wall. A plurality of vertical dividers is cut from the rear side wall and bent so as to be generally perpendicular to and extending forward from the rear side wall. Each of the vertical dividers includes a plurality of divider slots. The method also includes bending the top wall and the bottom wall so as to be generally perpendicular to and extending forward from the rear side wall, thereby defining a storage space accessible through an open front side of the housing. A horizontal shelf is engaged with the plurality of vertical dividers by sliding the horizontal shelf into the divider slots until an angled front portion of the shelf is wedged into frictional engagement with the divider slots. The frictional engagement holds the horizontal shelf in position such that the shelf and the plurality of vertical dividers split the storage space into a grid of box receptacles configured to receive the storage boxes.

In one aspect, the horizontal shelf further includes a blocking lip extending upwardly from the shelf at a rear edge. The method further includes inserting the horizontal shelf into the housing until the blocking lip abuts the rear side wall of the housing. The method may also include bending first and second end walls from the flat sheet of material so as to be generally perpendicular to and extending forward from the rear side wall. The first and second end walls are then coupled to the top wall and to the bottom wall such that the housing defines a box-shaped storage space. In another aspect, the method also includes removing the horizontal shelf from engagement with a first set of the divider slots in the plurality of vertical dividers and engaging the horizontal shelf with a second set of the divider slots in the plurality of vertical dividers. This repositioning of the shelf causes a reconfiguration of the vertical height of the box receptacles formed in the storage space.

These and other objects and advantages of the present invention will become more readily apparent during the following detailed description taken in conjunction with the drawings herein.

BRIEF DESCRIPTION OF THE DRAWINGS

The accompanying drawings, which are incorporated in and constitute a part of this specification, illustrate an embodiment of the invention and, together with a general description of the invention given above, and the detailed description of the embodiment given below, serve to explain the principles of the invention.

DETAILED DESCRIPTION

With reference to the figures, and more specifically to FIGS. 1 through 6, an exemplary embodiment is shown of a side access storage rack 10 used to hold storage boxes 12 (alternatively, "micro plates") within a cold storage unit 14 or a similar cryogenic vessel. Although the term "cold storage unit" is used throughout the specification, it will be understood that the side access storage rack 10 disclosed herein may be used with any type of cooling device, including refrigerators, freezers, and cryogenic vessels of any variety, collectively referred to hereinafter as "cold storage units." The storage boxes 12 typically contain a grid (not shown) or other internal structure for receiving and orienting a plurality of vials 16 or tubes filled with biological samples in an array. However, the storage boxes 12 may be sized to receive other types of containers for biological samples. As shown in the environment of the cold storage unit 14 in FIG. 1, the storage rack 10 is configured to be pulled partially out of a cooled interior space 18 through an opening 20 normally covered in operation by a door 22. Once the storage rack 10 is pulled partially through the opening 20, the storage boxes 12 held within the storage rack 10 may be accessed through an open front side 24 of the storage rack 10. The storage rack 10 includes a housing 26 defining a storage space 28 accessible via the open front side 24, the storage space 28 being divided into a plurality of box receptacles 30 by a plurality of vertical dividers 32 and a plurality of horizontal shelves 34. The horizontal shelves 34 of this exemplary embodiment are configured to be wedged into frictional engagement with the vertical dividers 32 to provide a storage rack 10 that is easier and quicker to assemble. Moreover, the horizontal shelves 34 are less susceptible to vibrations compared to the conventional storage rack designs described above, which improves the operation and the appearance of quality to a user.

Throughout the following description, directional and orientation terms such as vertical, horizontal, top, bottom, front, and rear are used to describe the relative relation of elements of the side access storage rack 10, as used in the exemplary embodiment within a cold storage unit 14. However, it will be appreciated that these terms are used for illustrative purposes only and do not limit the storage rack 10 to formation and use in such orientations. For example, the side access storage rack 10 may be manufactured or stored within a cold storage unit in other orientations depending on the needs of the user.

Figure 1:
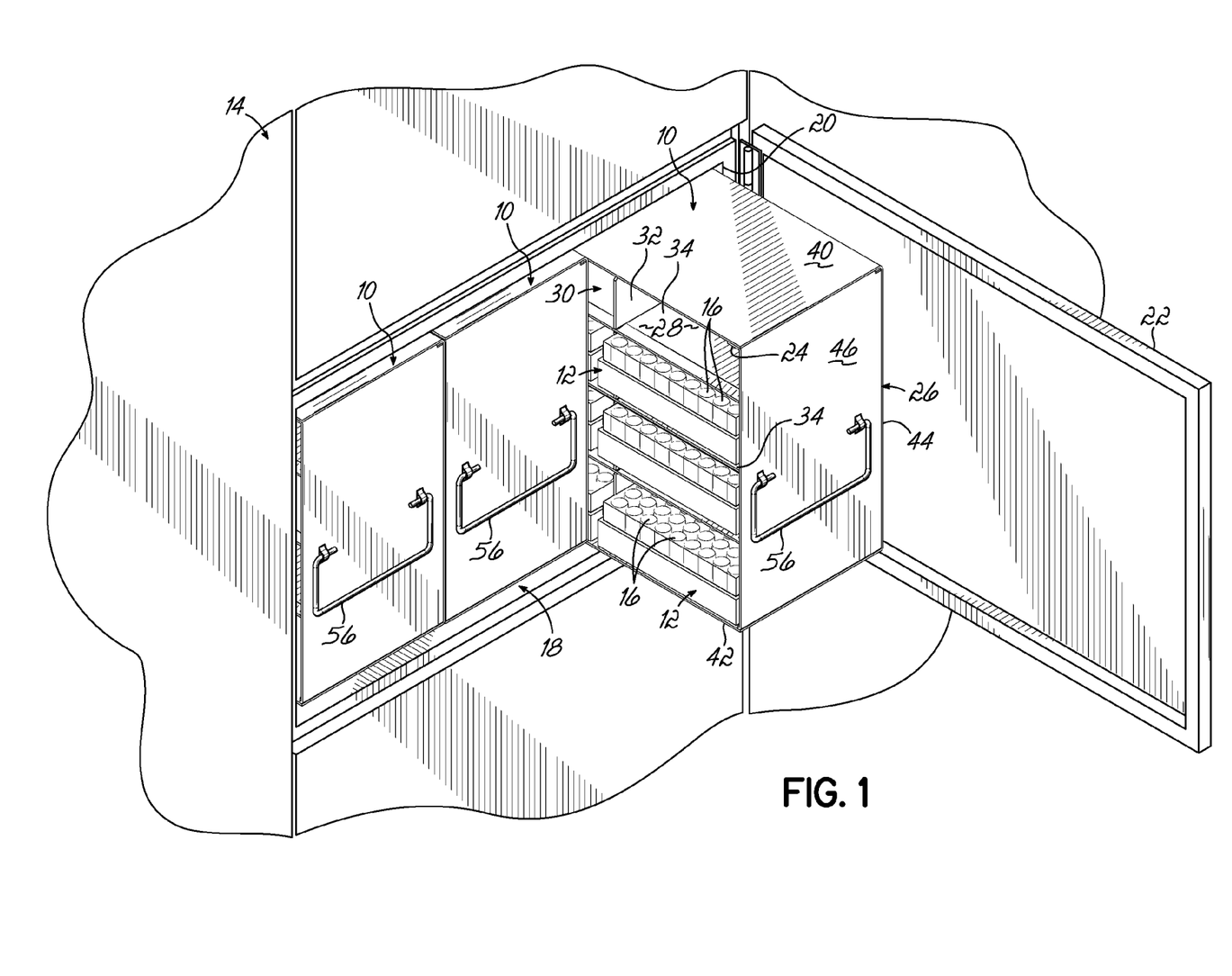
FIG. 1 is a perspective view of a cold storage unit including an exemplary embodiment of a side access storage rack according to the invention, with one of the side access storage racks partially pulled through an opening of the cold storage unit to illustrate the storage boxes held on the storage rack.
Figure 2:
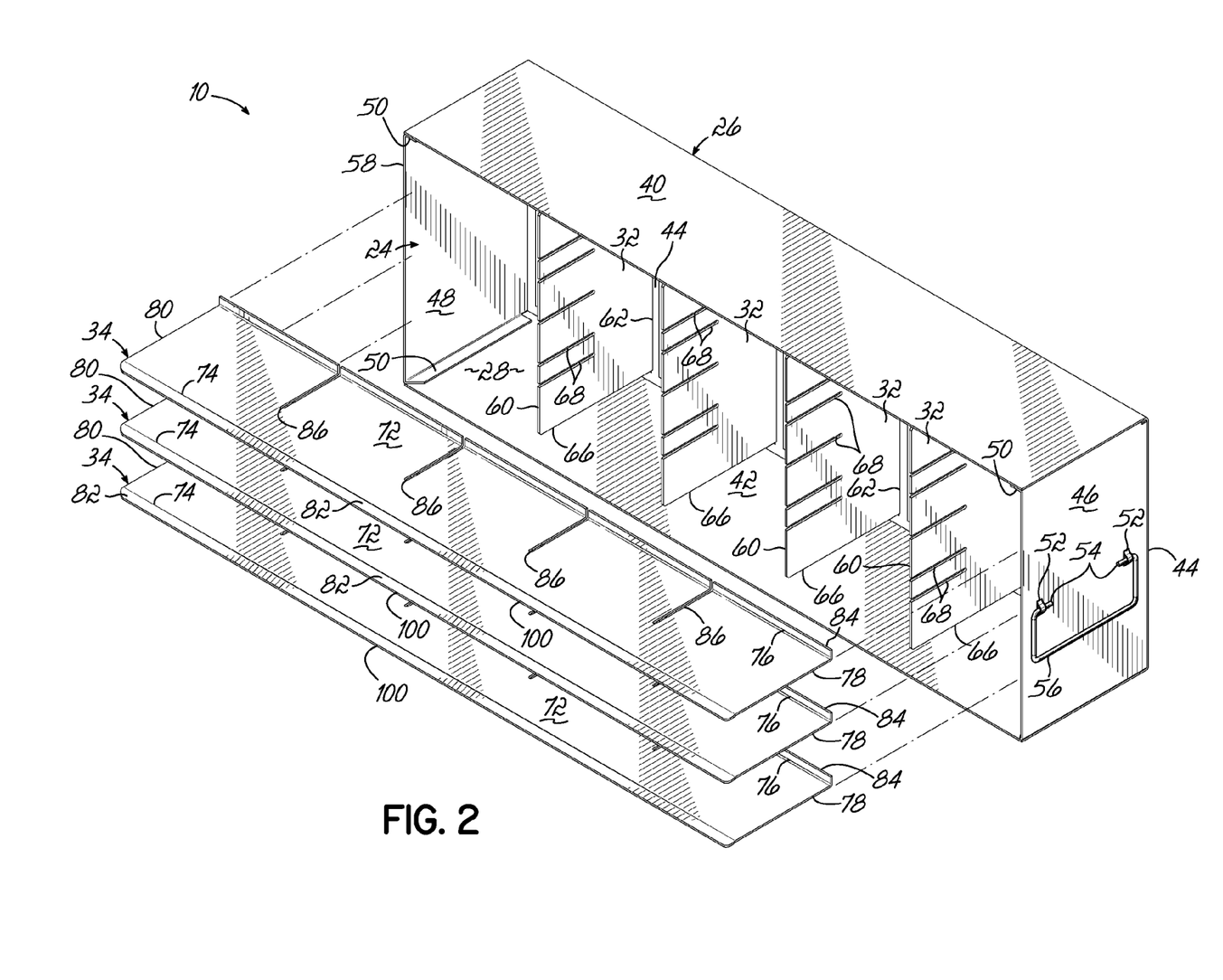
FIG. 2 is a partially exploded perspective view of one of the side access storage racks shown in FIG. 1, with a plurality of horizontal shelves separated from a housing.
Figure 3:
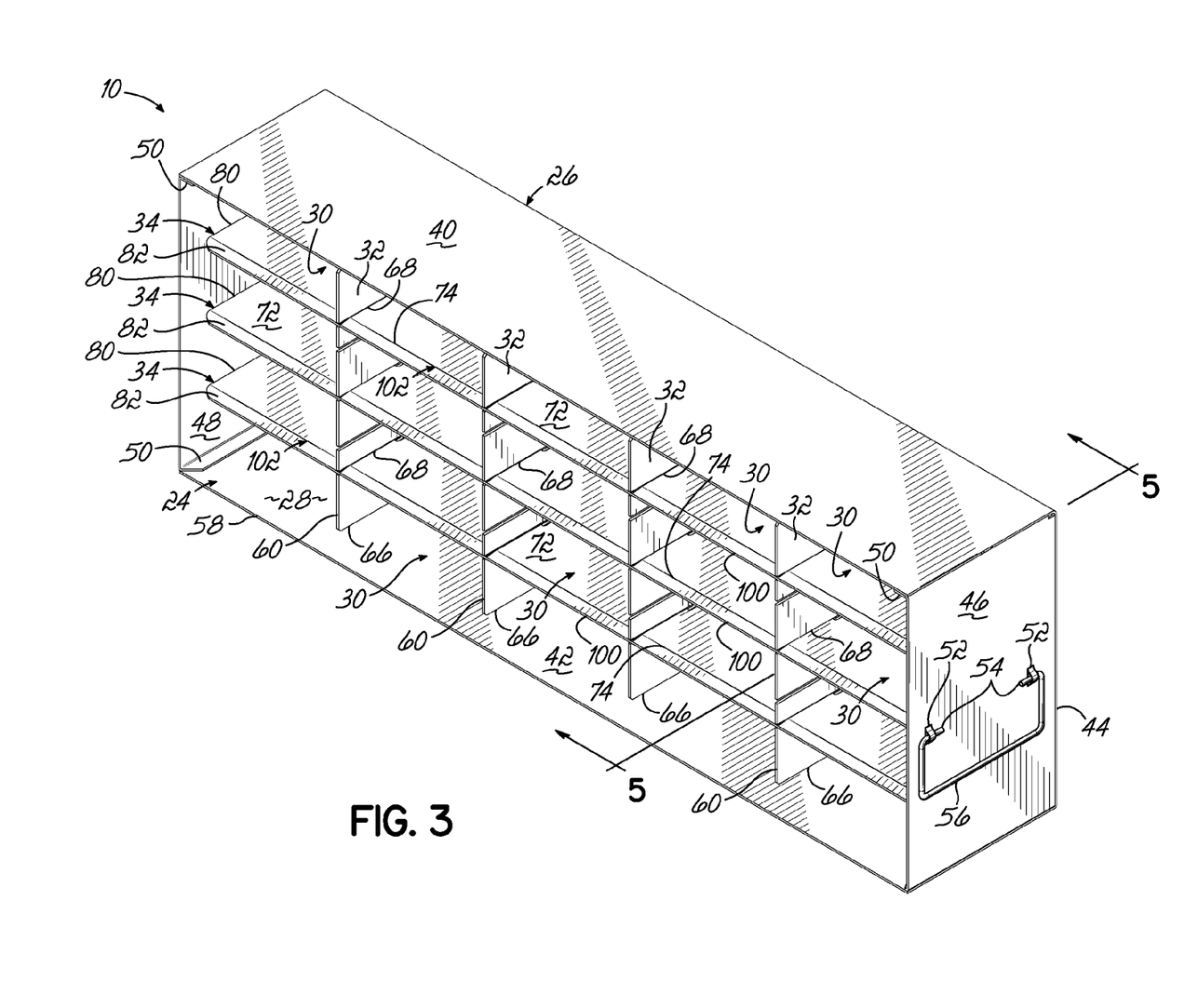
FIG. 3 is a perspective view of the side access storage rack of FIG. 2, with three horizontal shelves inserted into the housing.

With reference to FIGS. 2 and 3, the side access storage rack 10 of the exemplary embodiment is shown with three horizontal shelves 34 removed in FIG. 2 and inserted into position in FIG. 3. No storage boxes 12 are shown in these Figures, such that further details of the storage rack 10 are readily visible. The housing 26 of the storage rack 10 is formed from a single sheet of stainless steel material that is bent and welded into final shape as described in further detail below with reference to FIG. 7. Although stainless steel provides the storage rack 10 with high levels of strength and rigidity for the weight of material used, it will be understood that other materials may be used to form the storage rack 10 in other embodiments consistent with the present invention.

The housing 26 includes a top wall 40 and a bottom wall 42 connected to one another by a rear side wall 44. The housing also includes first and second end walls 46, 48 extending from opposing sides of the rear side wall 44. The top wall 40, bottom wall 42, and first and second end walls 46, 48 are bent from the rear side wall 44 so as to extend generally perpendicular to the rear side wall 44 and so as to extend towards the open front side 24. The first and second end walls 46, 48 also include connection flaps 50 bent into parallel and abutting relation with the corresponding top wall 40 and bottom wall 42. The connection flaps 50 are spot welded to the top wall 40 and the bottom wall 42 to form the generally box-shaped storage space 28 defined by the walls 40, 42, 44, 46, 48 of the housing 26. It will be understood that the connection flaps 50 may be provided on the top and bottom walls 40, 42 in other embodiments consistent with the scope of the present invention, and also that the connection flaps 50 may be adhered with adhesive or coupled by other known methods other than spot welding in still other embodiments.

The first end wall 46 includes a pair of pivotal hinge joints 52 configured to receive opposing ends 54 of a regular U-shaped fold-down handle 56. Each of the hinge joints 52 may be formed by punching a portion of the first end wall 46 outwardly from the storage space 28 or by connecting a separate joint member to the first end wall 46. The opposing ends 54 of the fold-down handle 56 are freely rotatable within the pivotal hinge joints 52 such that the handle 56 may be rotated from the stowed position alongside the first end wall 46 as shown in FIG. 2 to an active position extending away from the first end wall 46 for gripping use by the user. As described briefly above, the fold-down handle 56 enables a user to move the side access storage rack 10 into and out of a cold storage unit 14 despite only initially having access to the substantially solid first end wall 46. The fold-down handle 56 also does not substantially impact the storage density of storage boxes 12 within the cooled interior space 18 of the cold storage unit 14 as a result of being rotated down into the stowed position. Although not shown in these Figures, it will be understood that the handle 56 may instead be coupled to the second end wall 48 or handles 56 may be provided on both of the first and second end walls 46, 48 in other embodiments consistent with the present invention, when the alternative positioning of these handle(s) 56 is desirable or necessary.

With the exception of the pivotal hinge joints 52 located along at least one of the first and second end walls 46, 48, the box-shaped periphery 58 defined by the top and bottom walls 40, 42 and the first and second end walls 46, 48 is substantially solid and free from apertures or other structural irregularities. In this regard, the top and bottom walls 40, 42 and the first and second end walls 46, 48 are each substantially solid, planar sheets of material except at the pivotal hinge joints 52. As a result, the housing 26 of the storage rack 10 defines a substantially continuous and smooth outer periphery 58 that improves the appearance of the storage rack 10. The housing 26 also does not include a plurality of weakened areas caused by cutouts or punched areas along the outer periphery 58. The housing 26 is therefore also easily and quickly assembled by merely bending the respective walls 40, 42, 44, 46, 48 into position and making the spot welds at the connection flaps 50 without a plurality of additional manufacturing processes or steps required.

With continued reference to FIGS. 2 and 3, the plurality of vertical dividers 32 and the plurality of horizontal shelves 34 are shown in further detail. Each of the vertical dividers 32 is formed by punching a portion out of the rear side wall 44 and bending those portions to be generally perpendicular to the rear side wall 44. After bending into this perpendicular orientation, each of the vertical dividers 32 defines a front edge 60 facing towards the open front side 24 of the housing 26, a rear edge 62 connected to the rear side wall 44, a top edge 64 facing towards the top wall 40, and a bottom edge 66 facing towards the bottom wall 42. Each vertical divider 32 is sized slightly smaller than the cross-sectional dimension of the storage space 28 such that the top edge 64 is spaced inwardly from the top wall 40, the bottom edge 66 is spaced inwardly from the bottom wall 42, and the front edge 60 is spaced inwardly from the open front side 24 (this spacing best seen in FIG. 5). As a result, the vertical dividers 32 are completely supported by the rear side wall 44 and do not require any additional manufacturing or fastening steps to couple the vertical dividers 32 to other elements of the housing 26.

Each of the vertical dividers 32 also includes a plurality of divider slots 68 extending rearwardly from the front edge 60. The divider slots 68 extend about halfway from the front edge 60 to the rear edge 62 in the exemplary embodiment. The divider slots 68 of the exemplary embodiment include a first set of divider slots 68a spaced apart by approximately two inches and a second set of divider slots 68b spaced apart by approximately three inches. As described in further detail below, the relative height of the box receptacles 30 formed by the vertical dividers 32 and the horizontal shelves 34 may be easily modified by inserting the horizontal shelves 34 into either the first set of divider slots 68a or the second set of divider slots 68b. The approximate two inch and three inch heights accommodate typically used storage boxes 12 of those two heights. It will be understood that more or fewer slots 68 and sets of slots 68a, 68b may be provided with any desired spacing between the slots 68 in other embodiments of the storage rack 10 without departing from the scope of the invention.

The horizontal shelves 34 are shown most clearly in the partially exploded view of FIG. 2. In this regard, each of the horizontal shelves 34 is formed from a generally planar sheet 72 including a front edge 74, a rear edge 76, and first and second ends 78, 80 extending between the front and rear edges 74, 76. The horizontal shelf 34 includes an angled front portion 82 that is bent downwardly from the plane defined by the remainder of the generally planar sheet 72 at the front edge 74. The horizontal shelf 34 also includes a blocking lip 84 connected to the rear edge 76 and bent to extend generally upward in a perpendicular orientation to the planar sheet 72. The functionality of the blocking lip 84 is described in further detail below. Each horizontal shelf 34 further includes a plurality of shelf slots 86 extending forwardly from the rear edge 76. The shelf slots 86 are sized and configured to receive the corresponding plurality of vertical dividers 32 when the horizontal shelves 34 are inserted as shown in FIG. 3. Similar to the divider slots 68, the shelf slots 86 are cut to extend about halfway from the rear edge 76 to the front edge 74 of the horizontal shelves 34. Thus, in the exemplary embodiment, when the horizontal shelves 34 are inserted completely into engagement with the vertical dividers 32, the shelf slots 86 are substantially filled with a solid portion of the vertical dividers 32 and the divider slots 68 are substantially filled with a solid portion of the horizontal shelves 34. It will be understood that the corresponding sizes of the divider slots 68 and the shelf slots 86 may be modified in other embodiments of the invention.

Figure 4:
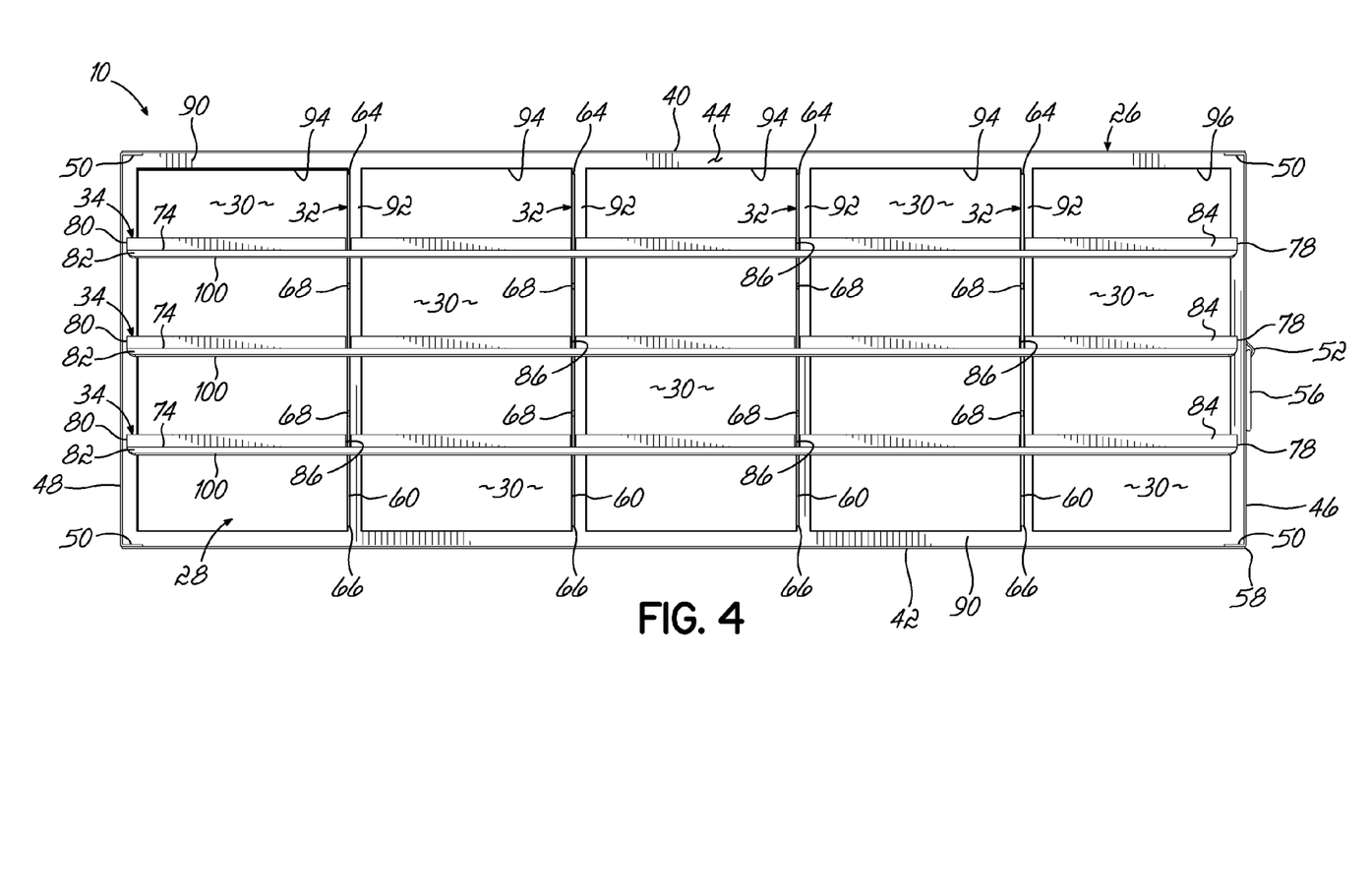
FIG. 4 is a front elevational view of the side access storage rack of FIG. 3.
Figure 5:
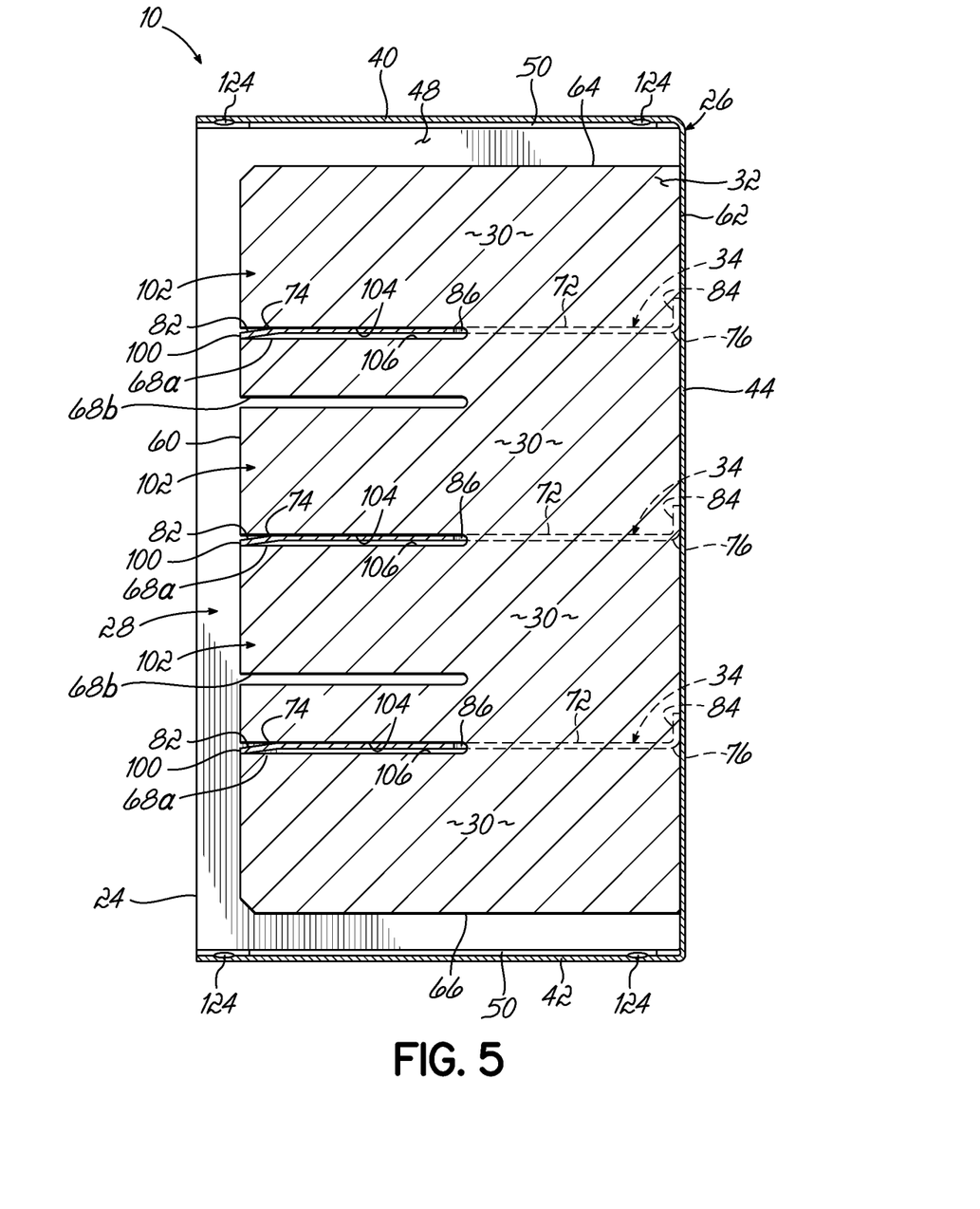
FIG. 5 is a cross-sectional side view of the side access storage rack of FIG. 3 along line 5-5 to show engagement of the horizontal shelves with vertical dividers in the housing.
Figure 6:
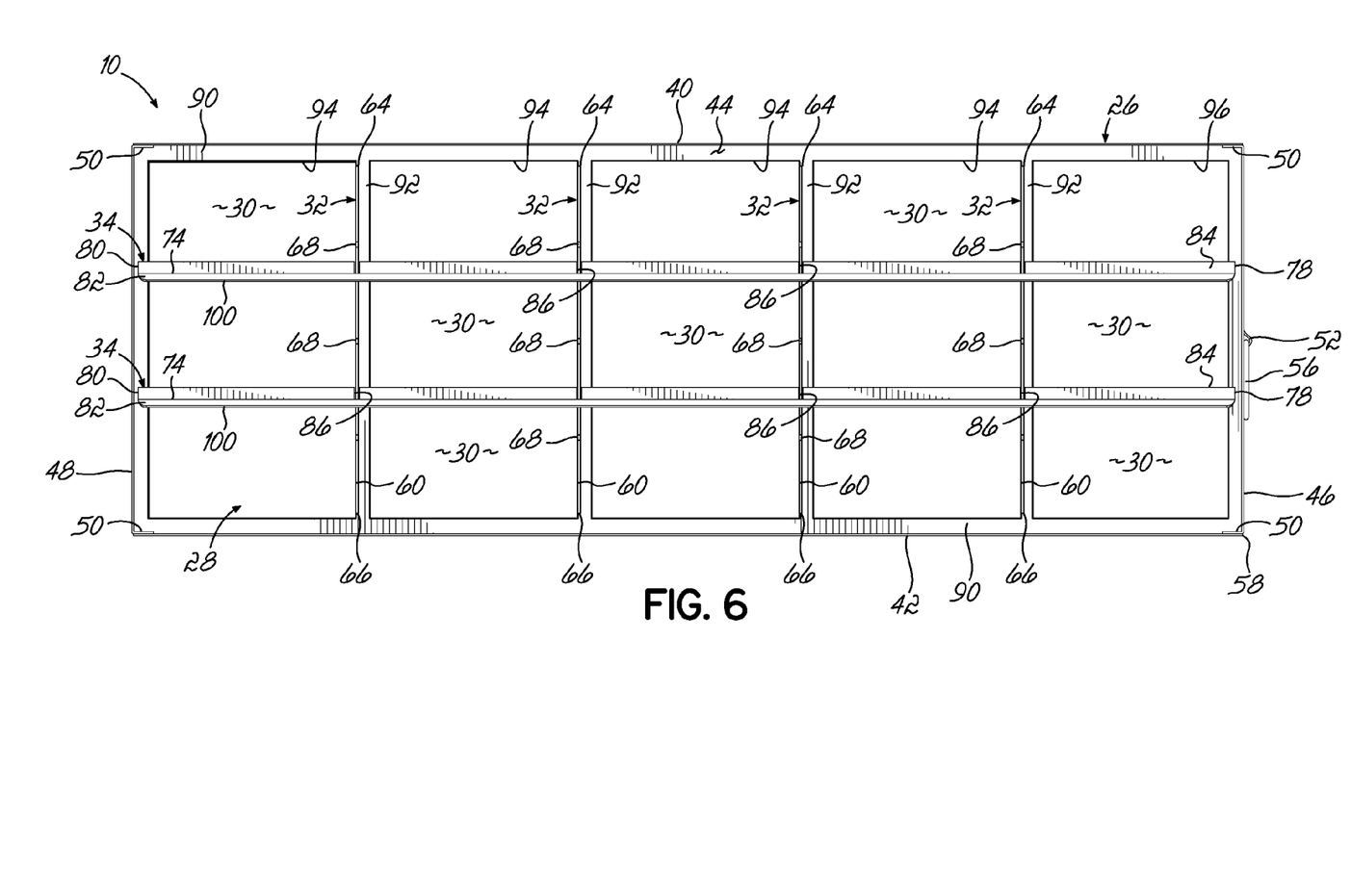
FIG. 6 is a front elevational view of the side access storage rack of FIG. 2, with only two horizontal shelves inserted into the housing to adjust the vertical height of box receptacles formed by the horizontal shelves and the vertical dividers.

The horizontal shelves 34 are shown in an engaged position with the vertical dividers 32 in FIGS. 3 through 5. With particular reference to FIGS. 3 and 4, the vertical dividers 32 and horizontal shelves 34 in combination form a grid-like structure that subdivides the box-shaped storage space 28 into the plurality of box receptacles 30, each sized to receive a storage box 12. The grid-like structure extends from the rear side wall 44 of the housing 26 without engaging the other elements of the housing 26. To this end, the first and second ends 78, 80 of each horizontal shelf 34 are spaced from the corresponding first and second end walls 46, 48 of the housing when the horizontal shelves 34 are inserted into the vertical dividers 32. Thus, contrary to the snap-in shelves described above for use with conventional side access storage racks, the horizontal shelves 34 are held in position and supported by only the vertical dividers 32 and the rear side wall 44.

As shown most clearly in FIG. 4, the rear side wall 44 defines an outer rectangular frame 90 with a plurality of intermediate vertical support columns 92 extending across the rectangular frame 90 between the apertures 94 formed by punching and bending the plurality of vertical dividers 32 from the rear side wall 44. The vertical support columns 92 directly support the vertical dividers 32 extending from the rear side wall 44. The rear side wall 44 may also include an additional aperture 96 located between the first end wall 46 of the housing and the vertical divider 32 closest to that first end wall 46. This additional aperture 96 does not form another vertical divider 32 because such a divider 32 is unnecessary at the first end wall 46. However, the material is still removed from the rear side wall 44 to make the rear side wall 44 uniform along the length of the housing 26 and also to reduce the total weight and material usage of the side access storage rack 10. The cutting and bending of this aperture 96 and the vertical dividers 32 from a planar sheet of material is further described in connection with the method of assembly described below (see FIG. 7).

The angled front portions 82 of the horizontal shelves 34 extend from the front edge 74 to a leading edge 100 configured to be located adjacent to the front edges 60 of the vertical dividers 32 when the shelves 34 are completely inserted as shown. To this end, the angled front portions 82 define a beveled opening 102 at the open front side 24 to assist with the insertion of storage boxes 12 into the box receptacles 30. It will be appreciated that the angled front portions 82 may be angled upwardly from the corresponding planar sheets 72 in alternative embodiments of the invention, which would enable the angled front portions 82 to serve as both the beveled opening 102 and as a further retaining mechanism for storage boxes 12.

Regardless of the specific angling of the angled front portions 82, the horizontal shelves 34 are reliably held in position by wedging the angled front portion 82 into frictional engagement with the divider slots 68 of the plurality of vertical dividers 32. This wedged frictional relationship between the horizontal shelves 34 and the vertical dividers 32 is more clearly illustrated in the cross-section shown in FIG. 5. The amount of angling defined by the angled front portion 82 is designed to be sufficient such that the front edge 74 of the generally planar sheet 72 is forced into engagement with an upper side 104 of the divider slot 68 while the leading edge 100 is forced into engagement with a lower side 106 of the divider slot 68. The frictional connection provides a plurality of rigid support or connection points along the length of each horizontal shelf 34. Consequently, the horizontal shelves 34 do not tend to vibrate due to long lengths between support points when the storage rack 10 is moved. The horizontal shelves 34 also have little contacting structure to vibrate against, as the shelves 34 are spaced from every element of the housing 26 except for the rear side wall 44 and the vertical dividers 32. Thus, the angled front portions 82 of the horizontal shelves 34 enable a frictional engagement of the shelves 34 with the vertical dividers 32 that is advantageous over conventional designs. More particularly, wedging the horizontal shelves 34 into frictional engagement with the vertical dividers 32 enables a rapid and reliable assembly of the side access storage rack 10.

With continued reference to FIGS. 4 and 5, the blocking lip 84 at the rear edge 76 of the horizontal shelves 34 is shown in position after the shelves 34 are inserted into the housing 26. In this regard, each horizontal shelf 34 is inserted into the corresponding divider slots 68 of the vertical dividers 32 until the blocking lip 84 abuts against one of the vertical support columns 92 or the outer rectangular frame 90 of the rear side wall 44. Because the blocking lip 84 projects upwardly from the remainder of the horizontal shelf 32 to occlude a portion of the apertures 94, 96 through the rear side wall 44, the blocking lip 84 is positioned to block sliding or twisting movement of the bottom end of storage boxes 12 through the rear side wall 44. Consequently, a user can push a storage box 12 into a box receptacle 30 until the storage box 12 abuts the blocking lip 84 and the storage box 12 will be prevented from sliding or twisting out of the storage rack 10 through the apertures 94, 96 of the rear side wall 44. This arrangement of blocking lips 84 renders the side access storage rack 10 easier to use because the user does not need to carefully align each storage box 12 manually with the box receptacle 30 and also does not need to be concerned about storage boxes 12 falling through the rear side wall 44. As a result, the only side of the side access storage rack 10 that a user must have access to in order to retrieve and replace the storage boxes 12 is the open front side 24 of the housing 26.

One additional benefit of the side access storage rack 10 of the exemplary embodiment is the ease with which the storage rack 10 may be reconfigured for different sizes of storage boxes 12. To this end, the horizontal shelves 34 may be removed and replaced into different positions quickly to modify the size and number of box receptacles 30 within the box-shaped storage space 28. For example, the horizontal shelves 34 may be moved from the configuration shown in FIGS. 4 and 5 (defining 20 box receptacles 30 for approximately two inch thick storage boxes 12) to the alternative configurations shown in FIG. 6 (defining 15 approximately box receptacles 30 for approximately 3 inch thick storage boxes 12). As described above and shown most clearly in FIG. 5, each of the vertical dividers 32 in the exemplary embodiment includes a first set of divider slots 68a that receive three horizontal shelves 34 in the configuration of FIGS. 4 and 5, and a second set of divider slots 68b that receive two horizontal shelves 34 in the configuration of FIG. 6. To switch between these configurations, a user has to only manually pull the horizontal shelves 34 out of the divider slots 68 against the frictional engagement and then manually insert the horizontal shelves 34 into frictional engagement with the new divider slots 68. No careful alignment and snapping engagement with tabs and projections is necessary, which significantly reduces the complexity and time required to modify the configuration of the side access storage rack 10. The horizontal shelves 34 have more rigidity than conventional designs when positioned in the vertical dividers 32 as a result of the angled front portion 82 and also as a result of the frictional engagement with the plurality of vertical dividers 32.

It will be understood that while two sets of divider slots 68a, 68b and two different configurations of the side access storage rack 10 are shown in the exemplary embodiment, the vertical dividers 32 may be reconfigured to provide any number of different sets of divider slots 68 as requested by the user. The bevel or angling of the angled front portion 82 on the horizontal shelves 34 is designed to provide sufficient friction to prevent accidental dislodging of the horizontal shelves 34 from the vertical dividers 32 during use of the storage rack 10 but not so much friction that the horizontal shelves 34 are highly difficult to remove and replace by a user during reconfiguration of the storage rack 10. Thus, the horizontal shelves 34 are inserted and removed from the storage rack 10 with a one-step simple linear sliding movement into or out of the vertical dividers 32.

Figure 7:
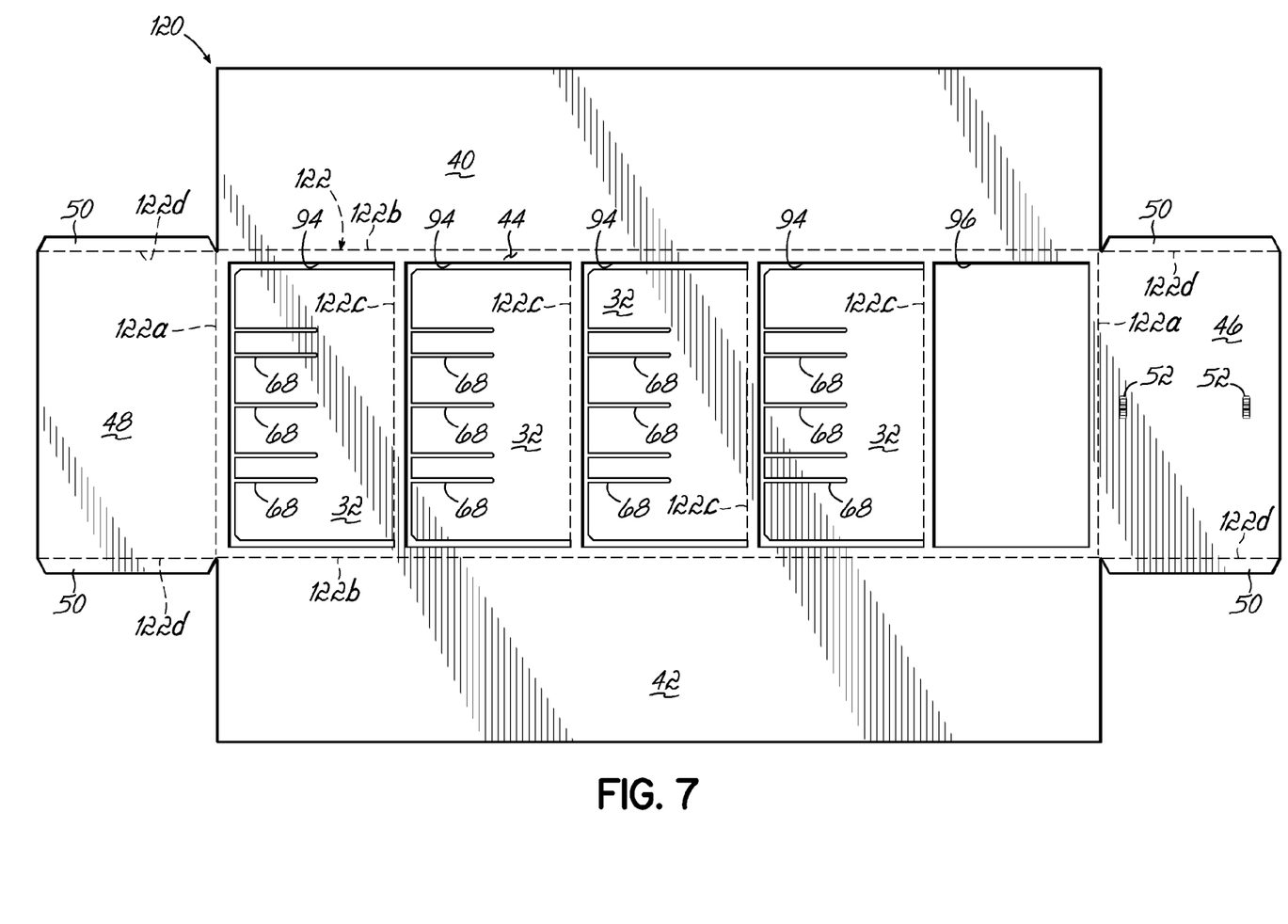
FIG. 7 is a top plan view of a sheet of material in the form of a blank used to form the housing and the vertical dividers of the side access storage rack shown in FIG. 2.

With reference to FIG. 7, the side access storage rack 10 of the exemplary embodiment is produced by the following manufacturing method. A flat sheet blank 120 (hereinafter "flat sheet" 120) is provided, the flat sheet 120 being sized to define the housing 26 including the top wall 40, bottom wall 42, rear side wall 44, and first and second end walls 46, 48. The flat sheet 120 is machined such as by punching or stamping to cut the vertical dividers 32 and the additional aperture 96 from the rear side wall 44. The flat sheet 120 may also be machined to include the pivotal hinge joints 52 in the first end wall 46 as previously described. From the state shown in FIG. 7, the first and second end walls 46, 48 are bent from the flat sheet 120 to be generally perpendicular to the rear side wall 44. The first and second end walls 46, 48 are bent along the bend lines 122a shown in phantom line form in FIG. 7. It will be understood that the bend lines 122 (including bend lines 122a, 122b, 122c, and 122d) may be scored on the flat sheet 120 prior to bending, although such scoring is not necessary in all embodiments of the present invention. The bend lines 122a are located between the first and second end walls 46, 48 and the rear side wall 44. Additionally, bend lines 122b are located between the top and bottom walls 40, 42 and the rear side wall 44, bend lines 122c are located between the vertical dividers 32 and the rear side wall 44, and bend lines 122d are located between the connection flaps 50 and the first and second end walls 46, 48. The flat sheet 120 is then further bent along bend lines 122b, 122c to bend the top wall 40, bottom wall 42, and the plurality of vertical dividers 32 into generally perpendicular orientation from the rear side wall 44. The connection flaps 50 on the first and second end walls 46, 48 are also bent along bend lines 122d so as to be in abutting relation with the top wall 40 and the bottom wall 42. As described above, each of the top wall 40, bottom wall 42, first and second end walls 46, 48, and vertical dividers 32 extends in the same direction towards the open front side 24 defined by the now box-shaped housing 26. It will be understood that the order of performing these bends along the various bend lines 122a, 122b, 122c, 122d may be performed in any order in other embodiments consistent with the scope of the current invention.

After these portions of the flat sheet 120 are bent into position, the connection flaps 50 of the first and second end walls 46, 48 are spot welded to the top and bottom walls 40, 42. These spot welds are shown schematically at reference number 124 in FIG. 5, for example. The fold-down handle 56 is then coupled to the housing 26 by inserting the opposing ends 54 of the handle 56 into the pivotal hinge joints 52 formed in the first end wall 46. The housing 26 is then in the finalized form shown in FIG. 2 and ready to receive one or more of the horizontal shelves 34. The horizontal shelves 34 are separately formed by bending the angled front portion 82 and the rear blocking lip 84 from a planar sheet of material 72 and then cutting the shelf slots 86 into the horizontal shelf 34. The horizontal shelves 34 are then inserted into the wedged frictional engagement with the divider slots 68 in the vertical dividers 32 to complete assembly of the side access storage rack 10. Each horizontal shelf 34 is inserted into the housing 26 until the blocking lip 84 of that shelf 34 abuts the rear side wall 44. As readily understood from the foregoing method, the storage rack 10 is manufactured and assembled using a minimal number of machining and manufacturing steps (e.g., only the connection flaps 50 require spot welding). This simplified process reduces the amount of time and manufacturing expense necessary to produce each side access storage rack 10. Moreover, the side access storage rack 10 provides easier reconfiguration of the box-shaped storage space 28 and a higher impression of quality as a result of the added rigidity and reduced vibrations present in the grid formed by the frictional engagement of the horizontal shelves 34 with the vertical dividers 32.

While the present invention has been illustrated by a description of an exemplary embodiment and while this embodiment has been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A side access storage rack for holding a plurality of storage boxes within a cold storage unit, comprising:
a housing including a top wall, a bottom wall, and a rear side wall defined by a single unitary sheet of material and extending between the top and bottom walls, the housing defining a storage space accessible through an open front side of the housing;
a plurality of vertical dividers extending from the rear side wall toward the open front side of the housing, each vertical divider including a front edge and a plurality of divider slots extending rearwardly from the front edge; and
a horizontal shelf including opposing front and rear edges, a plurality of shelf slots extending forwardly from the rear edge, and an angled front portion defined by a generally planar lip that is bent adjacent to the front edge from a remainder of the horizontal shelf,
wherein the horizontal shelf is engaged with the plurality of vertical dividers when the horizontal shelf is slid into the divider slots and the vertical dividers are slid into the shelf slots, such that the angled front portion of the horizontal shelf is received within the divider slots and wedges into frictional engagement with the divider slots, wherein the frictional engagement holds the horizontal shelf in position such that the horizontal shelf and the plurality of vertical dividers split the storage space into a grid of box receptacles configured to receive the storage boxes, and
wherein the rear side wall includes an outer frame and a plurality of support columns extending across the outer frame to define a plurality of apertures through the rear side wall, the plurality of apertures through the rear side wall being formed when the plurality of vertical dividers are punched out of the rear side wall and bent to be generally transverse to the rear side wall, and wherein the horizontal shelf further includes a blocking lip extending upwardly from the shelf at the rear edge, the blocking lip configured to block twisting or sliding movement of the storage boxes through the plurality of apertures in the rear side wall of the housing.

2. The side access storage rack of claim 1, wherein the angled front portion of the horizontal shelf is bent downwardly from the shelf such that the angled front portion defines a beveled opening for guiding storage boxes into the box receptacle.

3. The side access storage rack of claim 1, wherein the housing further includes first and second end walls extending between the top and bottom walls at opposing edges of the rear side wall to thereby define the storage space as box-shaped.

4. The side access storage rack of claim 3, wherein the angled front portion of the horizontal shelf includes a rear edge connected to the remainder of the horizontal shelf and a front edge defining a terminal end of the horizontal shelf, such that the frictional engagement between the horizontal shelf and the divider slots of the vertical dividers is defined by direct engagement of the front and rear edges of the angled front portion with opposite sides of each corresponding divider slot, and wherein the horizontal shelf is spaced from each of the first and second end walls when inserted into frictional engagement with the plurality of vertical dividers such that the horizontal shelf is completely supported by the frictional engagement with the plurality of vertical dividers.

5. The side access storage rack of claim 3, wherein a handle for manually moving the side access storage rack is pivotally coupled to one of the first and second end walls, and wherein the top wall, the bottom wall, and the first and second end walls are each formed as solid planar members except at the pivotal coupling of the handle to the first or second end wall.

6. The side access storage rack of claim 3, wherein the top wall, the bottom wall, the rear side wall, the first and second end walls, and the plurality of vertical dividers are defined by a single unitary sheet of material.

7. The side access storage rack of claim 1, comprising:
a plurality of horizontal shelves each including opposing front and rear edges, a plurality of shelf slots extending forwardly from the rear edge, and an angled front portion that is bent adjacent to the front edge,
wherein the horizontal shelves may be inserted into different sets of the plurality of divider slots in the vertical dividers to reconfigure the vertical height of the box receptacles formed in the storage space.

8. A cold storage unit for storing a plurality of storage boxes, comprising:
a cabinet having an opening with a door and defining a cooled interior space; and
at least one side access storage rack inserted into the cooled interior space through the opening, each side access storage rack including:
a housing including a top wall, a bottom wall, and a rear side wall defined by a single unitary sheet of material and extending between the top and bottom walls, the housing defining a storage space accessible through an open front side of the housing;
a plurality of vertical dividers extending from the rear side wall toward the open front side of the housing, each vertical divider including a front edge and a plurality of divider slots extending rearwardly from the front edge; and
a horizontal shelf including opposing front and rear edges, a plurality of shelf slots extending forwardly from the rear edge, and an angled front portion defined by a generally planar lip that is bent adjacent to the front edge from a remainder of the horizontal shelf,
wherein the horizontal shelf is engaged with the plurality of vertical dividers when the horizontal shelf is slid into the divider slots and the vertical dividers are slid into the shelf slots, such that the angled front portion of the horizontal shelf is received within the divider slots and wedges into frictional engagement with the divider slots, wherein the frictional engagement holds the horizontal shelf in position such that the horizontal shelf and the plurality of vertical dividers split the storage space into a grid of box receptacles configured to receive the storage boxes, and
wherein the rear side wall includes an outer frame and a plurality of support columns extending across the outer frame to define a plurality of apertures through the rear side wall, the plurality of apertures through the rear side wall being formed when the plurality of vertical dividers are punched out of the rear side wall and bent to be generally transverse to the rear side wall, and wherein the horizontal shelf further includes a blocking lip extending upwardly from the shelf at the rear edge, the blocking lip configured to block twisting or sliding movement of the storage boxes through the plurality of apertures in the rear side wall of the housing.

9. The cold storage unit of claim 8, wherein the angled front portion of the horizontal shelf is bent downwardly from the shelf such that the angled front portion defines a beveled opening for guiding storage boxes into the box receptacle.

10. The cold storage unit of claim 8, wherein the housing further includes first and second end walls extending between the top and bottom walls at opposing edges of the rear side wall to thereby define the storage space as box-shaped.

11. The cold storage unit of claim 10, wherein the angled front portion of the horizontal shelf includes a rear edge connected to the remainder of the horizontal shelf and a front edge defining a terminal end of the horizontal shelf, such that the frictional engagement between the horizontal shelf and the divider slots of the vertical dividers is defined by direct engagement of the front and rear edges of the angled front portion with opposite sides of each corresponding divider slot, and wherein the horizontal shelf is spaced from each of the first and second end walls when inserted into frictional engagement with the plurality of vertical dividers such that the horizontal shelf is completely supported by the frictional engagement with the plurality of vertical dividers.

12. The cold storage unit of claim 10, wherein a handle for manually moving the side access storage rack into and out of the cooled interior space is pivotally coupled to one of the first and second end walls, and wherein the top wall, the bottom wall, and the first and second end walls are each formed as solid planar members except at the pivotal coupling of the handle to the first or second end wall.

13. The cold storage unit of claim 10, wherein the top wall, the bottom wall, the rear side wall, the first and second end walls, and the plurality of vertical dividers are defined by a single unitary sheet of material.

14. The cold storage unit of claim 8, wherein each side access storage rack comprises:
 a plurality of horizontal shelves each including opposing front and rear edges, a plurality of shelf slots extending forwardly from the rear edge, and an angled front portion that is bent adjacent to the front edge,
 wherein the horizontal shelves may be inserted into different sets of the plurality of divider slots in the vertical dividers to reconfigure the vertical height of the box receptacles formed in the storage space.

* * * * *